(12) United States Patent
Msika et al.

(10) Patent No.: US 10,092,495 B2
(45) Date of Patent: Oct. 9, 2018

(54) USE OF A COMPOSITION COMPRISING AVOCADO PERSEOSE IN THE PROTECTION OF EPIDERMAL STEM CELLS

(71) Applicant: LABORATOIRES EXPANSCIENCE, Courbevoie (FR)

(72) Inventors: Philippe Msika, Versailles (FR); Caroline Baudouin, Rambouillet (FR)

(73) Assignee: LABORATOIRE EXPANSCIENCE, Paris la Defense (FR)

( * ) Notice: Subject to any disclaimer, the term of this patent is extended or adjusted under 35 U.S.C. 154(b) by 37 days.

(21) Appl. No.: 14/766,602

(22) PCT Filed: Feb. 11, 2014

(86) PCT No.: PCT/EP2014/052665
§ 371 (c)(1),
(2) Date: Aug. 7, 2015

(87) PCT Pub. No.: WO2014/122326
PCT Pub. Date: Aug. 14, 2014

(65) Prior Publication Data
US 2015/0374605 A1 Dec. 31, 2015

Related U.S. Application Data

(60) Provisional application No. 61/763,294, filed on Feb. 11, 2013.

(30) Foreign Application Priority Data

Feb. 11, 2013 (FR) ..................................... 13 51136

(51) Int. Cl.
| | | |
|---|---|---|
| *A61K 31/7024* | (2006.01) | |
| *A61K 8/60* | (2006.01) | |
| *A61K 31/22* | (2006.01) | |
| *C07C 69/02* | (2006.01) | |
| *C07C 69/52* | (2006.01) | |
| *C07C 69/533* | (2006.01) | |
| *A61K 31/232* | (2006.01) | |
| *C07C 69/587* | (2006.01) | |
| *A61K 31/23* | (2006.01) | |
| *A61Q 19/00* | (2006.01) | |
| *A61Q 19/08* | (2006.01) | |
| *A61K 45/06* | (2006.01) | |
| *A61K 31/7012* | (2006.01) | |
| *A61K 36/54* | (2006.01) | |
| *A61K 8/97* | (2017.01) | |
| *A61Q 5/02* | (2006.01) | |
| *A61Q 17/04* | (2006.01) | |
| *A61Q 19/10* | (2006.01) | |

(52) U.S. Cl.
CPC .................. *A61K 8/60* (2013.01); *A61K 8/97* (2013.01); *A61K 31/22* (2013.01); *A61K 31/23* (2013.01); *A61K 31/232* (2013.01); *A61K 31/7012* (2013.01); *A61K 31/7024* (2013.01); *A61K 36/54* (2013.01); *A61K 45/06* (2013.01); *A61Q 19/00* (2013.01); *A61Q 19/004* (2013.01); *A61Q 19/005* (2013.01); *A61Q 19/08* (2013.01); *C07C 69/02* (2013.01); *C07C 69/52* (2013.01); *C07C 69/533* (2013.01); *C07C 69/587* (2013.01); *A61Q 5/02* (2013.01); *A61Q 17/04* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 7,897,579 B2 * | 3/2011 | Piccirilli | .................. | A61K 8/60 514/23 |
| 8,349,377 B2 * | 1/2013 | Piccirilli | .............. | A61K 31/198 424/725 |
| 9,023,810 B2 * | 5/2015 | Piccirilli | .................. | A61K 8/60 514/23 |
| 2007/0280918 A1 * | 12/2007 | Schwartz | ............... | A61K 31/00 424/94.2 |

(Continued)

FOREIGN PATENT DOCUMENTS

| | | | |
|---|---|---|---|
| WO | WO095/03809 | * 2/1995 | ............. A61K 31/70 |
| WO | WO 2005/115421 A1 | 12/2005 | |
| WO | WO 2011/073281 A1 | 6/2011 | |

(Continued)

OTHER PUBLICATIONS

Merriam-Webster's Collegiate Dictionary, published 1998 by Merriam-Webster, Incorporated, p. 924.*
Leclere-Bienfait et al., "Avocado perseoue, a biomimetic active ingredient for the protection and accompaniment of infants' skin," Journal of Investigative Dermatology, p. S106, May 1, 2013 (Abstract).
International Search Report issued in application No. PCT/EP2014/052665 dated Apr. 14, 2014.
Mills et al., "Pediatric Melanoma: A Review," Cancer Control, vol. 16, No. 3, pp. 225-233, Jul. 2009.

(Continued)

*Primary Examiner* — Eric Olson
(74) *Attorney, Agent, or Firm* — Potomac Law Group, PLLC

(57) ABSTRACT

The invention concerns a use of C7 sugars and derivatives of formula (I), called avocado perseose, which have, inter alia, a protective activity to epidermal skin cells. These C7 sugars and derivatives are capable of maintaining the expression of markers of adult stem cells, in particular basal stem cells. Avocado perseose can also be used for preventing the deleterious effects of environmental damage. Avocado perseose has a beneficial effect on the conservation of the potential of epidermal stem cells and thus helps maintain skin homeostasis.

33 Claims, 3 Drawing Sheets

(56) References Cited

U.S. PATENT DOCUMENTS

Figure 1:
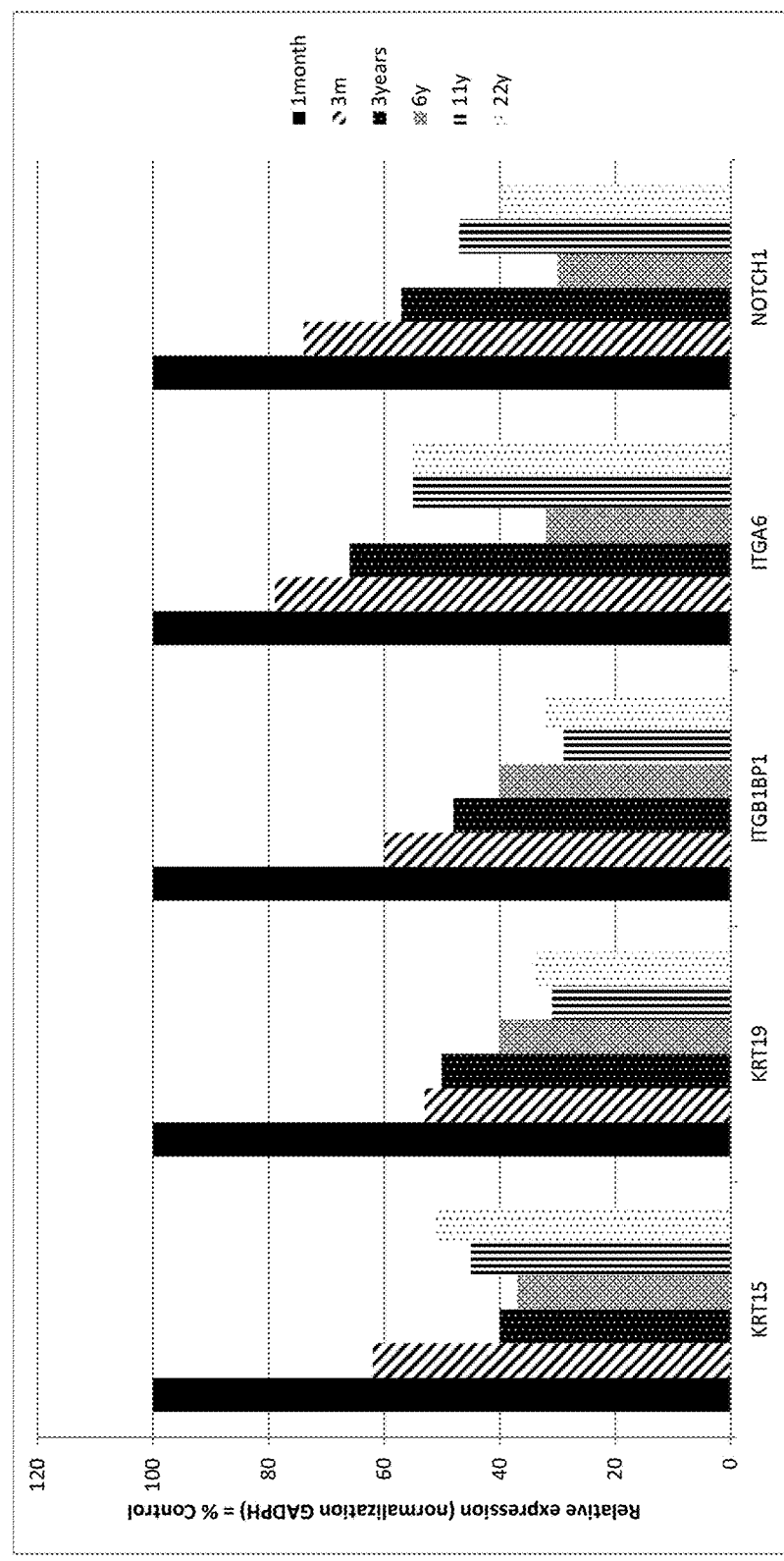

2013/0004444 A1* 1/2013 Baudouin ................ A61K 8/60
424/61
2016/0084822 A1* 3/2016 Msika .................. G01N 33/502
435/6.12

FOREIGN PATENT DOCUMENTS

WO    WO 2010/085224 A1    6/2012
WO    WO 2012/123774 A1    9/2012

OTHER PUBLICATIONS

Board et al., "High Km Glucose-phosphorylating (Glucokinase) Activities in a Range of Tumor Cell Lines and Inhibition of Rates of Tumor Growth by the Specific Enzyme Inhibitor Mannoheptulose," Cancer Research, vol. 55, pp. 3278-3285, Aug. 1995.
Bredif et al., "Avocado Sugars are Effective Inducers of Cutaneous Defensive Functions," Journal of Investigative Dermatology, vol. 126, p. s52, 2006 (Abstract).

\* cited by examiner

USE OF A COMPOSITION COMPRISING AVOCADO PERSEOSE IN THE PROTECTION OF EPIDERMAL STEM CELLS

INTRODUCTION

With a surface area of about 2 m², the skin is the largest organ of the human body (about 16% of total body weight). Its principal function is to establish a protective barrier against environmental insults while allowing some exchanges between the internal medium and the external medium. It is the location of many metabolic processes modulated by the physiological conditions of the organism and the conditions of the environment. The skin is made of two joined layers: the epidermis and the dermis, with which the subcutaneous tissues are associated.

The epidermis constitutes the outermost structure of the skin. Its principal role is the protection of the body: it ensures the impermeability of the skin and its resistance. This tissue is in particular made up of a pluristratified epithelium, called the interfollicular epithelium, whose role is notably to provide a barrier function with respect to the environment. The interfollicular epithelium consists of four distinct cellular layers, a basal layer (*stratum basalis*), a spinous layer (*stratum spinosum*), a granular layer (*stratum granulosum*) and a corneal layer (*stratum corneum*).

Although various cell types coexist in the epidermis, keratinocytes comprise the large majority (90%). Their characteristic activity is the synthesis of keratins, which account for 95% of the total proteins of the epidermis.

However, the *stratum corneum*, which is the layer protecting the skin against external insults (heat, cold, dehydration, etc.), is composed of specific cells, corneocytes, which are completely flat cells, without a nucleus or cytoplasmic organelles, and are the result of the terminal phase of keratinocyte differentiation. The *stratum corneum* is more particularly divided into two distinct layers, one where the corneocytes are still connected to each other via corneodesmosomes, and another where, under the action of specific enzymes, the corneodesmosomes break down, enabling the corneocytes to become detached, a process called desquamation. This process takes part in the continuous renewal of the epidermis.

Adaptation to extrauterine life is a process that begins at birth and continues throughout the first year of life. The first months of postnatal life constitute a period of structural and functional reorganization of the skin which enables physiological adaptation to the extrauterine environment. For example, the immaturity of the skin of a newborn is underlined by the different structure and molecular composition of its *stratum corneum* compared to that of an adult. These are incomplete and thus continue to develop during the first 12 months at least after birth (Chiou et al., *Skin Pharmacol Physiol*, 17: 57-66, 2004; Nikolovski et al., *J Invest Dermatol*, 128: 1728-1736, 2008; Stamatas et al., *Pediatr Dermatol*, 27: 125-131, 2010).

Furthermore, the results of a recent clinical study (Fluhr et al., *Br J Dermatol*, 166(3): 483-90, 2012) suggest that the skin of infants has a certain immaturity in its capacity to capture water and to regulate the related mechanisms, which will have an impact on the quality and the competence of the barrier function.

An incomplete skin maturation can have significant clinical consequences. It is thus important to enable the skin to be built and to develop correctly and harmoniously, while maintaining its functional and structural organization. In this respect, it is crucial to preserve the capacity of renewal of the epidermis.

The interfollicular epidermis is a dynamic tissue that undergoes constant renewal, roughly every 28 day on average. On the other hand, the *stratum corneum* is completely renewed every 15 days. The maintenance of the integrity of the epidermis is closely related to the biology of the keratinocytes constituting its basal layer. Epidermal homeostasis results indeed from a finely regulated equilibrium between proliferation and differentiation of the basal keratinocytes, which makes it possible to ensure the physiological renewal of the tissue, as well as its regeneration when damaged. More particularly, the regenerative capacity of the epidermis is conferred by adult stem cells which enable the regular replacement of the differentiated cells eliminated during keratinization. This process is in particular crucial for the maturation and the maintenance of the barrier function.

Adult stem cells are undifferentiated but specialized cells that can be defined by two principal properties: their ability to self-renew and to remain in place for very long periods, but also their ability to generate all the types of differentiated cells of the tissue in question, which defines their multipotency. This latter property may be absent in certain adult stem cells; on the other hand, all types of adult stem cells have a high potential of proliferation in the long term. To these two principal characteristics is added a certain quiescence of these cells. These cells divide relatively infrequently and only under the influence of precise and probably specific stimuli from the tissue in which they are located. The division, known as asymmetrical division, will yield two daughter cells with distinct fates. The first will be a stem cell identical to the mother cell, which will be bestowed with the same characteristics (self-renewal and multipotency) and which will enter in quiescence. On the other hand, the second cell will enter the cell cycle and divide actively a certain number of times while losing its multipotent nature, before committing definitely to a differentiation pathway.

The skin, as an organ undergoing rapid and continuous renewal, thus belongs to tissues that host a significant number of stem cells or cells already engaged in a specific cell line. The skin contains, among others, melanocyte stem cells (which yield melanocytes) located in the pilous follicles and in the basal layer of the epidermis, so-called SKP cells, which express nestin, at the neural level, dermal/mesenchymal stem cells in conjunctive tissue, adipose-derived stem cells in adipose tissue, and epidermal stem cells.

Epidermal stem cells reside in an area called the "bulge" of the pilous follicle (follicular stem cells), in the sebaceous glands (sebaceous stem cells) and in the basal layer of the epidermis (interfollicular epidermal stem cells) (Dahl, *J Cosmet Dermatol*, 11: 297-306, 2012; Eckert et al., *Biochim Biophys Acta*, 1830: 2427-2434, 2013). In addition to forming the keratinocytes generating the epidermis and its barrier function (*stratum corneum*), epidermal stem cells also form the follicles of the hair and the sebaceous glands and related structures.

The major reservoir of epidermal stem cells is the basal layer, which contains stem cells that ensure the renewal of the keratinocytes of the epidermis. Indeed, these stem cells give birth by asymmetrical division to transit amplifying cells, which are committed to definitive differentiation after dividing three to five times. The following stage of differentiation of the transit amplifying cells generates postmitotic basal keratinocytes (PMD) which divide no further and starts the process of differentiation and migration while moving away from the basal membrane (Fuchs, *J Cell Biol,* 182(2): 273-284, 2008). These processes are finely controlled and regulated in relation to the processes of proliferation, differentiation and desquamation.

Stem cells reside in a specialized microenvironment that helps maintain the stem cell phenotype. This microenvironment, called a stem cell "niche," creates a biochemical, structural and spatial context that influences cell division and differentiation. Each niche is generally comprised of stem cells, transit amplifying cells, macromolecules of the extracellular matrix, signaling molecules and other factors (Dahl, *J Cosmet Dermatol,* 11: 297-306, 2012).

Epidermal stem cells help maintain the homeostasis of the epidermis. They must ensure the integrity of the tissue throughout its life by regenerating the layers of skin cells subjected to the process of differentiation. They are also essential for the phenomena of scarring and repair of the epidermis when injured. But, a loss of control of the asymmetry of the divisions can deplete the pool of stem cells, which leads to scarring defects and degenerative changes associated with aging (Dahl, *J Cosmet Dermatol,* 11: 297-306, 2012). Moreover, over time, stem cells lose their stem potential and the skin ages (Dereure, *Ann Dermatol Venereol.* 139(8-9): 568-578, 2012). The aging of these cells is accelerated by extrinsic factors such as pollution and UV rays. The protection of stem cells is thus essential to limit external insults. More generally, it is thus crucial for the good health of the skin to preserve intact the potential of stem cells and, in particular, their ability to self-renew.

DESCRIPTION

The inventors have found that, surprisingly, the C7 sugars and derivatives of formula (I), called avocado perseose and which will be defined below, have, among others, a protective activity for epidermal stem cells. These C7 sugars and derivatives are able in a surprising way to maintain the expression of markers for adult stem cells, notably basal stem cells. These compounds have a beneficial effect on the conservation of the potential of epidermal stem cells and, thus, help maintain the homeostasis of the skin.

The invention relates to the use of avocado perseose to protect epidermal stem cells and, in particular, basal stem cells.

In particular, avocado perseose makes it possible to prevent the deleterious effects of environmental insults.

The term "environmental insults" as used herein refers to all of the environmental conditions that exert a severe constraint on the skin and affect its natural process of construction, evolution and maturation.

Such conditions include, for example, heating and air-conditioning, wind, exposure to the sun, and the resulting UV irradiation, and environmental pollution. On this subject, it should be noted that certain conditions can affect the natural process of construction, evolution and maturation of the skin by accelerating said process. But it is also possible that certain experimental conditions limit this process (see, for example, Valacchi et al., *Ann. N.Y. Acad. Sci.,* 1271: 75-81, 2012). In fact, the harmful effects on the skin of these environmental insults are well described. These deleterious environmental insults can disrupt the development of the skin, and in particular of the epidermis and of certain of its structures and functions, such as the barrier function, which become organized after birth. Aggressive environmental conditions thus lead to changes in cutaneous structure and functions which translate in the long term to a certain fragility, reactivity, wrinkles, loss of firmness and elasticity, dryness, burns, superficial or more significant wounds and other undesirable cosmetic effects.

The inventors have shown that the exposure of the skin to aggressive environmental conditions leads to a loss of the potential of stem cells. In particular, the markers defining stem cells and, in particular, basal stem cells, are no longer observed when the skin is subjected to such environmental insults. However, the inventors have shown that, surprisingly, the C7 sugars of the invention are capable of protecting epidermal stem cells from the deleterious action of these insults. In particular, the inventors have noted that the C7 sugars found in avocado, perseitol and mannoheptulose, as well as derivatives thereof resulting from the esterification of one or more of the hydroxyl functional groups of the sugar advantageously with a fatty acid, maintain the expression of markers defining epidermal stem cells in skin, while at the same time the skin undergoes aggressive environmental conditions, which demonstrates that said sugars are capable of protecting the potential of epidermal stem cells and, more particularly, that of basal stem cells.

On the other hand, these same avocado sugars do not affect the expression of markers for epidermal stem cells in skin that has not been subjected to environmental insults such as UV radiation, which suggests that said sugars are tolerated perfectly by the unstressed organism. In fact, they are so well tolerated that no difference in expression of said markers could be detected in the absence of environmental insult. Indeed, the stem cell markers expression profile detected by the inventors in skin of various ages is maintained in the presence of the avocado sugars of the invention.

These compounds are thus perfectly neutral for the skin in the absence of insult, but, at the same time, are capable of restoring the ability of stem cells, including, in particular, basal stem cells, in attacked skin, such as, for example, irradiated skin. More generally, the C7 sugars of the invention accompany the development and the organization of the skin after birth by preserving stem cells. Thus, these compounds preserve the ability of the skin, and in particular children's skin, to resist the deleterious effects of environmental insults.

According to a first aspect, the invention relates to the cosmetic use of a composition including at least one C7 sugar or derivative of the following formula (I)

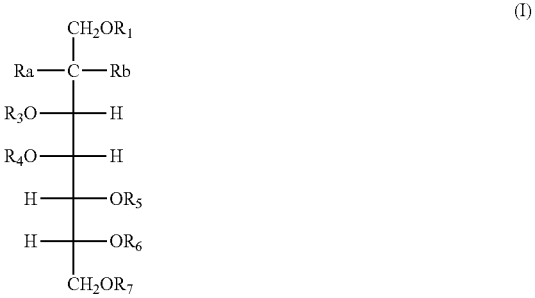

in which

Ra represents a hydrogen atom and Rb represents an —OR$_2$ or CRaRb represents the CO radical;

R$_1$, R$_2$, R$_3$, R$_4$, R$_5$, R$_6$ and R$_7$ represent, independently of one another
 a hydrogen atom or
 a —(CO)—R radical in which R represents a saturated or unsaturated hydrocarbon chain containing from 11 to 24 carbon atoms, optionally substituted by one or more substituents selected from the group comprised of hydroxy radicals (—OH), ethoxy radicals (—OC$_2$H$_5$) and the —SO$_3$M group with M representing a hydrogen atom, an ammonium ion (NH$_4^+$) or a metal ion; or a —(CO)—R' radical in which R' represents a saturated or unsaturated hydrocarbon chain containing from 2 to 10 carbon atoms, optionally substituted by one or more substituents selected from the group comprised of hydroxy radicals (—OH), ethoxy radicals (—OC$_2$H$_5$) and the —SO$_3$M group with M representing a hydrogen atom, an ammonium ion (NH$_4^+$) or a metal ion;

and a pharmaceutically acceptable excipient for the protection of epidermal stem cells and, in particular, basal stem cells.

According to a preferential embodiment of the invention, the composition prevents the deleterious effects for the skin of environmental insults. According to this embodiment, the invention relates to the cosmetic use of a composition including at least one C7 sugar or derivative of the formula (I) and a pharmaceutically acceptable excipient for the prevention of the deleterious effects for the skin of environmental insults, wherein that said composition protects epidermal stem cells and, in particular, basal stem cells.

As has long been known to persons skilled in the art, the *stratum corneum* plays an essential role within the skin by its structure and its contact with the external medium. It thus constitutes the skin's principal barrier against environmental insults, whether physical (UV rays, etc.), chemical (cosmetic products, etc.) or mechanical (cuts, pinching, etc.). It is important in this respect to remark that, for this function to be exercised correctly, it is essential that the *stratum corneum* is present in its integrity: absent that, the overall permeability of the skin increases. In particular, it is important to maintain the regular cellular renewal of this layer.

In a more preferential embodiment, the invention is thus directed to the cosmetic use of the composition for preserving the barrier function. According to this embodiment, the invention is directed to a cosmetic use of a composition including at least one C7 sugar or derivative of the formula (I) and a pharmaceutically acceptable excipient for the preservation of the barrier function of the skin, wherein said composition protects epidermal stem cells and, in particular, basal stem cells.

It is well known that UV rays are the principal factor for extrinsic aging of the skin (see, for example, Passeron and Ortonne, *Presse Med* 32: 1474-1482, 2003), either by direct interaction with cellular DNA (the principal mode of action of UVB), or indirectly by means of active forms of oxygen (the principal mode of action of UVA).

During the aging process, various characteristic signs appear on the skin, which are reflected in particular in a change in cutaneous structure and function with, e.g., a deterioration of the barrier function. The existing signs of aging, more particularly the photo-induced signs, are in particular lines and wrinkles whose appearance increases with age and which are observed as depressions or furrows on the surface of the skin. Other signs of cutaneous aging, which result from a dysfunction of the principal biological mechanisms intervening on the level of the skin, appear as, e.g., desquamation, a change in tone, a tarnishing to be specific, and by surface roughness and dryness.

According to a more preferential embodiment of the invention, the composition is used to prevent the aging of the skin. According to this embodiment, the invention is directed to a cosmetic use of a composition including at least one C7 sugar or derivative of the formula (I) and a pharmaceutically acceptable excipient for the prevention of the aging of the skin, wherein said composition protects epidermal stem cells and, in particular, basal stem cells.

Furthermore, difficult environmental conditions often give rise to the appearance of wounds. It is thus important that the skin is able to heal correctly. A "scar" as used herein refers to the part of the tissue that constitutes the closing of wounds and, in particular, losses of small and/or large portions of tissues and organs. Scar tissue is in fact formed at each interruption of the continuity of the skin (epidermis and/or dermis) caused by a pathological or traumatic event due to environmental insults.

Epidermal stem cells and, in particular, basal stem cells, participate in the general homeostasis of the skin and are necessary to the scarring process. Indeed, their division makes it possible to sufficiently generate differentiated cells in order to constitute the scar.

According to another more preferential embodiment, the composition of the invention promotes the scarring of the skin. According to this embodiment, the invention is directed to a cosmetic use of a composition including at least one C7 sugar or derivative of the formula (I) and a pharmaceutically acceptable excipient to promote the scarring of the skin, wherein said composition protects epidermal stem cells and, in particular, basal stem cells.

It is also well-known that environmental insults are at the source of many cancers. Thus, UV rays, because of their genotoxic properties, have an important role in the induction and development of skin cancers. Exposure to UV rays may target stem cells in the skin of children, which would increase the risks of skin cancer in adulthood (Volkmer and Greinert, *Prog Biophys Mol Biol*, 107(3): 386-8, 2011). It is thus important to preserve the potential of stem cells and, in particular, basal stem cells, in order to prevent the occurrences of cancer at a later stage of life.

In a second aspect, the invention provides a composition including at least one C7 sugar or derivative of the formula (I) and a pharmaceutically acceptable excipient for use in the prevention of cancer, preferably skin cancer, wherein said composition protects epidermal stem cells and, in particular, basal stem cells.

In other words, according to this embodiment, the invention relates to the use of a composition including at least one C7 sugar or derivative of the formula (I) and a pharmaceutically acceptable excipient for the manufacture of a drug to prevent cancer, preferably skin cancer, wherein said composition protects epidermal stem cells and, in particular, basal stem cells.

It is understood that the cosmetic or therapeutic compositions of the invention are used in mammals, and preferably in humans. More preferentially, said compositions are used in children. The term "child" as used in the invention refers to an individual younger than 16 years of age. The category of "children" according to the invention thus includes newborns, between 0 and 1 month of age, infants, between 1 month and 2 years of age, and actual children, who are at least 2 years old. A "newborn", as used herein, may be a full-term birth or may be premature.

To eliminate any ambiguity, the term "child" as used in the present application without any further information should be understood in its most general meaning, i.e., as referring to a person younger than 16 years of age. An "adult" in the context of the present invention is a person who is not a child, i.e., a person older than 16 years of age.

D-mannoheptulose, the first ketoheptose identified in 1916 by La Forge, of the general formula (II)

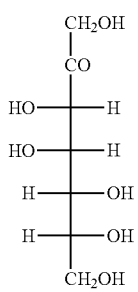

(II)

is found in certain plants, in particular in alfalfa (*Medicago sativa* L.), in avocado, in fig (*Ficus officinalis* L.), in yellow arsenic (*Sedum spectabile* Bor.) and in primula (*Primula officinalis* Jacq.). However, it is in avocado that the highest concentrations of D-mannoheptulose are found. D-mannoheptulose has already been used in therapeutic applications. For example, the patent application WO 95/03809 describes the use of D-mannoheptulose as a glucokinase inhibitor in order to inhibit the development of tumor cells and the application US 2003/0092669 describes an oral dietary supplement including D-mannoheptulose which makes it possible to decrease insulin levels and which thus enables weight loss.

Perseitol, the polyol form of D-mannoheptulose, of the general formula (III)

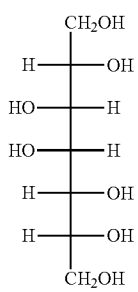

(III)

is also found in avocado, in particular in avocado fruit or seed.

It has been shown that perseitol, associated with a potassium ion, makes it possible to inhibit the incorporation of $^3$H-leucine in Ehrlich ascites tumor cells (Shibuya et al., *Pure Appl. Chem.*, 71(6): 1109-1113, 1999).

The use of these sugars (perseitol and D-mannoheptulose) to stimulate the synthesis of human beta-defensins (in particular HBD-2) has already been described (WO 2005/115421). The use of these sugars in the treatment of candidiasis and *pityriasis* has also been described (WO 2008/025847). Finally, it has been shown that these sugars could be used to treat alopecia (WO 2011/073281).

On the other hand, it has never been shown that C7 sugars could protect the stem cells of the epidermis and, in particular, the basal stem cells.

The term "stem cell of the epidermis" or "epidermal stem cell" as used in the present invention refers to a cell of the epidermis capable of long-term renewal.

The epidermal stem cells of the invention include, among others, follicular stem cells, sebaceous stem cells and basal stem cells, the latter being also called interfollicular epidermal stem cells. The terms "follicular stem cells," "sebaceous stem cells" and "basal stem cells" as used in the invention refer to stem cells located in the region of the bulge of the pilous follicle, in sebaceous glands and in the basal layer of the epidermis, respectively. In a preferential embodiment of the invention, the epidermal stem cells of the invention are basal stem cells.

More precisely, the term "epidermal stem cell" as used in the present invention refers to a cell bestowed with a high potential for long-term renewal. The term "potential of renewal" as used herein refers to the ability to undergo at least one cell division cycle. A "high potential for long-term renewal" thus represents the ability of a cell to enter several successive cell division cycles. It is well-known that the differentiated cells of the skin are unable to carry out several successive divisions (Fortunel and Martin, *J Soc Biol*, 202 (1): 55-65, 2008). It is understood herein that "successive" does not mean "consecutive" and that there may be periods during which a stem cell according to the invention remains quiescent without however losing its high potential for long-term renewal.

The conservation of a high potential for long-term renewal is expressed by an asymmetrical division producing two different cells. The first daughter cell is a stem cell identical to the mother stem cell, whereas the second is a transit-amplifying cell which divides in a limited fashion over a short period and then enters the differentiation process. Advantageously, the epidermal stem cells of the invention are thus furthermore able to generate at least one type of epidermal cell by differentiation. In other words, the transit amplifying cell is able to give rise to at least one type of epidermal cell by differentiation. Preferentially, said epidermal cell is a keratinocyte. More preferentially, the transit amplifying cell is able to give rise to all the types of epidermal cells by differentiation.

As will have been noted, the definition of the stem cells of the invention is above all functional, since it rests on the property via which these cells keep the ability to divide for very a long period of time. However, it may be difficult to verify if a cell possesses such a property, in particular when said cell is included in one or more layers of cells, e.g. in natural skin (for example in an organism), in a reconstituted skin model, a monolayer or bilayer culture, etc.

It is thus advantageous to be capable of identifying epidermal stem cells on the basis of other criteria. More precisely, it has been shown that it is particularly advantageous to use markers to identify stem cells.

According to this preferred embodiment of the invention, avocado C7 sugars and compositions containing same make it possible to maintain the expression of one or more stem cell markers, notably those for basal stem cells.

A "marker" according to the invention is a substance or a distinct biochemical, genetic or molecular characteristic that is specific to epidermal stem cells. For example, it is known that the dye Hoechst 33342 (Sigma-Aldrich) is actively exported by the epidermal stem cells (Larderet et al., *Stem Cells* 24(4): 965-974, 2006).

Advantageously, the "marker" according to the invention is specifically present in said epidermal stem cells. In other words, in this case, the "marker" according to the invention is expressed preferentially in epidermal stem cells. Alternatively, the term "marker" as used herein also encompasses the genes and proteins that exhibit a specific absence of expression in epidermal stem cells.

The expression of a marker is maintained by avocado C7 sugars and compositions containing same if the expression level of said marker is not affected by said sugars or composition. In other words, the C7 sugars and the compositions lead to a substantially identical level of expression of the marker in a cell treated with said sugars or compositions and in an untreated cell.

Advantageously, avocado C7 sugars and compositions including same make it possible to maintain the expression of a marker for an epidermal stem cell, regardless of the age of the donor of said stem cell.

Preferably, avocado C7 sugars and compositions including same make it possible to maintain the expression of a stem cell of the epidermis subjected to an environmental insult when the expression level of a marker in this epidermal stem cell attacked and treated with said sugars or composition is substantially identical to the level of said marker in a control epidermal stem cell. More preferably, said control epidermal stem cell is an epidermal stem cell that has not been subjected to environmental insult.

More preferably, avocado C7 sugars and compositions including same make it possible to maintain the expression of a stem cell of the epidermis irradiated with UV radiation when the expression level of a marker in this epidermal stem cell irradiated and treated with said sugars or composition is substantially identical to the level of said marker in a control epidermal stem cell. More preferably, said control epidermal stem cell is an epidermal stem cell that has not been irradiated.

The marker according to the invention is preferably a gene marker, a protein marker, a lipid marker or a metabolic marker. For each of these types of markers, numerous methods are available to persons skilled in the art to measure the expression of said marker and thus to identify a difference in expression between the epidermal stem cells and the other cells of the skin.

In a first embodiment, said marker is a gene marker or a protein marker. A specific gene or protein marker for epidermal stem cells is a gene or a protein, respectively, expressed differentially in stem cells. For example, such a gene or protein marker can be preferentially expressed in said stem cells or its expression can be specifically inhibited in said stem cells.

Such markers have been described in numerous publications (Larderet et al., *Stem Cells* 24(4): 965-974, 2006; Cambiaso et al., *Keratin,* 13: 9-15, 2007; Fortunel and Martin, J Soc Biol, 202(1): 55-65, 2008; Craig et al., *Mol Cancer,* 9: 195-207, 2010; Dereure, *Ann Dermatol Venereol.* 139(8-9): 568-578, 2012; Dahl, J Cosmet Dermato, 11: 297-306, 2012) and are thus well-known to persons skilled in the art.

Examples of markers include ΔNp63, survivin, FN1 (fibronectin 1), MCSP (melanoma-associated chondroitin sulfate proteoglycan), LRIG1 (leucine-rich repeats and immunoglobulin-like domains protein 1), GJA1 (connexin 43), NID1 (nidogen 1), KRT15 (keratin 15), KRT19 (keratin 19), EGFR (epidermal growth factor receptor), CD71 (transferrin receptor), DSG3 (desmoglein 3), ITGB1BP1 (integrin beta1 binding protein), ITGA6 (integrin alpha 6) and ITGB4 (integrin beta 4), as well as markers involved in the signaling and regulation of stem cell activity such as Wnt/beta catenin, sonic hedgehog (SHH) and NOTCH1 (notch homolog 1, translocation-associated). ΔNp63 and survivin are markers of resistance to apoptosis, thus having a role in stem cell survival. Cytokeratins 15 and 19 are positive stem cell markers, cytokeratin 15 being a marker for their survival. MCSP colocalizes with integrins in cells that do not divide, whereas integrin beta 1 (marker for adhesion to the extracellular matrix of the basal membrane) and integrin alpha 6 (constituting hemidesmosomes, marker for keratinocytes binding together) are surface proteins that take part in intercellular communication, regulating the differentiation/proliferation processes as well as interaction with the niche. Transferrin receptor (CD71) is a known surface marker for stem cells which is used to isolate, in a population of integrin alpha 6-positive cells, cells with high clonogenic capacity. Finally, LRIG1 is an epidermal growth factor receptor (EGFR) antagonist, thus maintaining quiescent stem cells, whereas EGFR, which is a marker whose absence characterizes stem cells, in contrast leads the cells down the proliferation pathway.

This list is not restrictive and persons skilled in the art will be able to identify other markers for stem cells of the epidermis and the niche on the basis of their general knowledge.

Preferentially, the gene or protein marker according to the invention is selected from among KRT15, NOTCH1, KRT19, ITGBP1 and ITGA6. Even more preferentially, said gene or protein marker according to the invention is ITGA6.

The composition including a C7 sugar will be thus able according to the invention to protect stem cells if it is capable of maintaining the expression of the gene or protein marker for said stem cells.

The expression of the gene or protein marker for the invention can be detected by any means known to persons skilled in the art.

Generally, the expression of the gene or protein marker according to the invention will be detected in vitro from a skin sample.

The term "skin sample" as used in the invention refers to any sample containing skin cells. The skin samples according to the invention thus further include explants of fresh skin obtained directly from the patient as well as skin cell cultures in suspension, monolayer skin cell cultures, bilayer skin cell cultures and tissue models, including cultures of reconstructed epidermis and skin and cultures of reconstructed mucosa. As it is often difficult to work with fresh explants, it is particularly advantageous, in the context of the present invention, to use skin cell cultures. Advantageously, the skin cells according to the invention include normal, healthy or pathological cells, or cells arising from cell lines. For example, cultured skin cells can be cells obtained from a skin tissue explant. The term "explant" or "skin explant" as used herein refers to a sampling of cells or skin tissue, which may be carried out in the context of a surgical procedure or to perform analyses.

In particular, an explant may be obtained during exeresis. The term "exeresis" as used herein refers to a surgical procedure consisting in cutting out (excising) a more or less broad or deep section of skin in order to treat an anomaly or an excrescence. An exeresis if performed either to remove a cancerous tumor or one suspected to be, or to treat a benign but troublesome anomaly of the skin, for either functional or esthetic reasons. An exeresis in the context of the invention includes, for example, skin samples obtained from plastic surgeries (mammaplasty, abdominoplasty, rhytidoplasty, circumcision, otoplasty, i.e., ear pinning, syndactyly or polydactyly, etc.).

An explant may also be obtained by biopsy. The term "biopsy" as used herein refers to a sampling of cutaneous cells or tissue for purposes of analysis. Several types of biopsy procedures are known and practiced in the field. The most common types include (1) incisional biopsy, in which only a sample of tissue is removed; (2) excisional (or surgical) biopsy, which consists in the total ablation of a tumor mass, thus carrying out a therapeutic gesture and diagnoses, and (3) needle aspiration biopsy, in which a sample of tissue is removed via a needle, which may be fine or large. Other types of biopsy exist, such as, for example, smears or scraping, and are also encompassed by the present invention.

In this case, the invention may comprise one or more intermediate steps between the sampling of the skin cells and the measurement of the expression of the biological marker may exist, said steps corresponding to the extraction from said sample of skin cells of a sample of mRNA (or of the corresponding cDNA) or of a sample of protein. This can then be used directly to measure the expression of the marker. The preparation and the extraction of mRNA (as well as the reverse transcription of mRNA into cDNA) or proteins from a cellular sample are routine procedures well-known to persons skilled in the art.

Once a sample of mRNA (or the corresponding cDNA) or protein is obtained, the expression of the marker, either in terms of mRNA (i.e., in all of the mRNA or cDNA present in the sample), or in terms of proteins (i.e., in all the proteins present in the sample), can be measured. The method used to accomplish this thus depends on the type of transformation (mRNA, cDNA or protein) and on the type of sample available.

When the expression of the marker is measured at the mRNA level (or the corresponding cDNA), any technology commonly used by persons skilled in the art may be used. These technologies for analyzing levels of gene expression, such as transcriptome analysis, for example, include well-known methods such as PCR (polymerase chain reaction, if starting with DNA), RT-PCR (reverse transcription PCR, if starting with RNA) and quantitative RT-PCR, or nucleic acid chips (including DNA chips and oligonucleotide chips) for a higher throughput.

The term "nucleic acid chips" as used herein refers to several different nucleic acid probes attached to a substrate, which may be a microchip, a glass slide, or a microsphere-size bead. The microchip may be composed of polymers, plastics, resins, polysaccharides, silica or a material containing silica, carbon, metals, inorganic glass or nitrocellulose.

The probes may be nucleic acids such as cDNA (cDNA chips), mRNA (mRNA chips) or oligonucleotides (oligonucleotide chips), said oligonucleotides typically having a length of between roughly 25 and 60 nucleotides.

To determine the expression profile of a particular gene, a nucleic acid corresponding to all or part of said gene is marked and then contacted with the chip under hybridization conditions, leading to the formation of complexes between said marked target nucleic acids and probes complementary to this nucleic acid attached to the surface of the chip. The presence of the marked hybrid complexes is then detected.

These technologies make it possible to follow the level of expression of one gene in particular or several genes, and even of all the genes of the genome (full genome or full transcriptome) in a biological sample (cells, tissues, etc.). These technologies are used routinely by persons skilled in the art and thus it is not necessary to detail them herein. Examples of implementations of the invention based on analysis of gene expression (cDNA chips) and on quantitative PCR are described in the experimental section.

Alternatively, it is possible to use any current or future technology making it possible to determine the expression of genes on the basis of the quantity of mRNA in the sample. For example, persons skilled in the art can measure the expression of a gene by hybridization with a marked nucleic acid probe, such as, for example, with a Northern blot (for mRNA) or a Southern blot (for cDNA), but also by techniques such as the serial analysis of gene expression (SAGE) method and its derivatives, such as LongSAGE, SuperSAGE, DeepSAGE, etc. It is also possible to use tissue chips (also known as tissue microarrays, or TMA5). The tests commonly employed with tissue chips include immunohistochemistry and fluorescent in situ hybridization. For the analysis of mRNA levels, tissue chips may be coupled with fluorescent in situ hybridization. Finally, it is possible to use massively parallel sequencing to determine the quantity of mRNA in the sample (RNA-Seq, or whole transcriptome shotgun sequencing). For that purpose, several methods of massively parallel sequencing are available. Such methods are described in, e.g., U.S. Pat. No. 4,882,127, U.S. Pat. No. 4,849,077; U.S. Pat. No. 7,556,922; U.S. Pat. No. 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure and Ji, *Nat Biotechnol.*, 26(10): 1135-45. 2008; Pihlak et al., *Nat Biotechnol.*, 26(6): 676-684, 2008; Fuller et al., *Nature Biotechnol.*, 27(11): 1013-1023, 2009; Mardis, *Genome Med.*, 1(4): 40, 2009; Metzker, *Natural Rev. Genet.*, 11(1): 31-46, 2010.

When the expression of the marker is measured at the protein level, it is possible to employ specific antibodies, in particular in well-known technologies such as immunoprecipitation, immunohistology, Western blot, dot blot, ELISA or ELISPOT, protein chips, antibody chips, or tissue chips coupled with immunohistochemistry. Other techniques that may be used include FRET or BRET techniques, methods of microscopy or histochemistry, notably including methods of confocal microscopy and electron microscopy, methods based on the use of one or more excitation wavelengths and a suitable optical method, such as an electrochemical method (voltammetry and amperometry techniques), atomic force microscopy, and radio frequency methods, such as multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, etc.), flow cytometry, radioisotope or magnetic resonance imaging, analysis by polyacrylamide gel electrophoresis (SDS-PAGE), HPLC-mass spectrometry and liquid chromatography-mass spectrophotometry/mass spectrometry (LC-MS/MS). All of these techniques are well-known to the skilled person and it is not necessary to detail them herein.

According to a first advantageous variant of the invention, the C7 sugars are in a free form (the hydroxyl functional groups are not esterified). The composition thus includes a C7 sugar selected from the group comprised of mannoheptulose, perseitol and mixtures thereof.

The source of D-mannoheptulose and/or perseitol may be a water-soluble extract of sugars from avocado or from another plant. Other than that, D-mannoheptulose and perseitol (of synthetic origin) are available commercially. According to an advantageous variant of the invention, the source of D-mannoheptulose and/or perseitol is a water-soluble extract of avocado sugars.

The water-soluble extract of avocado sugars may be obtained directly from any part of the avocado or the avocado tree, such as the fruit, the peel, the seed, the leaves or the roots of the avocado tree. It is also possible to obtain a water-soluble extract of sugars from the by-products of the avocado processing industry, among which mention may be made, in a non-exhaustive way, of: fresh avocado flesh, frozen pulp, dehydrated pulp, avocado oil cakes resulting from oil extraction processes (mechanical extraction and/or by solvent from previously dehydrated fruit), de-oiled solid matter resulting from wet oil extraction processes (so-called centrifugation process), de-oiled solid matter resulting from enzymatic avocado oil extraction processes, raw avocado purees (guacamole), solid waste from the facilities that produce these purees. The extract is advantageously obtained from the fresh fruits of the avocado tree. The fruits may be selected from among the Hass, Fuerte, Ettinger, Bacon, Nabal, Anaheim, Lula, Reed, Zutano, Queen, Criola Selva, Mexicana Canta, Region Dschang, Hall, Booth, Peterson and Collinson Redn varieties, more advantageously among the Hass, Fuerte and Reed varieties. Preferably, the Hass, Fuerte, Ettinger and Bacon varieties will be selected, and more advantageously the Hass and Fuerte varieties.

The fruit of the avocado tree is mainly composed of water, flesh, oil and seed. The proportions of these components are, like all natural and plant matter, highly variable. However, the average composition data presented in the following table 1, expressed as a percentage fresh fruit, are generally accepted:

TABLE 1

| Water | 70-85% |
|---|---|
| Proteins | 1.5-4.5% |
| Lipids | 12-23% |
| Sugars | 1.5-5% |
| Fibers | 1.1-1.6% |

In fact, the avocado is not particularly saccharide-rich. However, the nature of soluble monosaccharides is quite particular, such as perseitol or D-mannoheptulose composed of seven carbon atoms.

The water-soluble extract of avocado sugars is likely to be obtained by a process including the following successive steps:
  obtaining an avocado oil cake, advantageously from the avocado fruit, by drying the avocado and then extracting the lipids (oil); then
  complete delipidation of said oil cake, then washing with water or a hydro-alcoholic medium and then decantation and centrifugation in order to recover a soluble C7 sugar-rich fraction (elimination of the cake);
  demineralization over an ionic resin of said soluble fraction obtained in the preceding step; then
  ultrafiltration at 10,000 daltons; and
  if need be, vacuum concentration and packaging.

The first step of the process consists in drying the fruit and then removing the oil. Thus, after the fruit is cut into thin slices, its can be dried by any of the techniques known to persons skilled in the art, among which mention may be made of hot air drying, lyophilization, dehydration using zeolites or osmotic drying. Generally, the temperature during this drying step will advantageously be maintained, regardless of the technique used, at or below 80° C. In the context of the present process, for reasons of ease of implementation and for reasons of cost, drying in ventilated driers, in thin layers and under a stream of hot air, at a temperature of between 70 and 75° C. is preferred. The duration of the operation may vary between 5 and 72 hours.

The lipids from the dried fruit are then extracted either mechanically in a continuous screw press, or chemically, using a solvent such as hexane, in a Soxhlet extractor or a continuous band extractor of the De Smet® type, notably according to the method described in the application FR 2 843 027, or by a process using supercritical $CO_2$. Among the main advantages of the process, the oil co-produced is a product with quite evident direct commercial potential. The dry and de-oiled fruit, also called oil cake, can then undergo the following steps:
  total delipidation, notably with acetone and/or ethanol,
  decanting then washing the oil cake with water and/or a water-alcohol mixture,
  removal of the cake by centrifugation, filtration, recovery of the soluble fraction,
  concentration,
  demineralization by ion exchange
  ultrafiltration with a 10 kDa cut-off,
  vacuum concentration, adding preservatives and packaging.

Generally, the final aqueous extract may contain by weight 0.1 to 20% dry matter, advantageously 1 to 10% dry matter, even more advantageously 3 to 5% dry matter. The proportion of C7 sugars, i.e., D-mannoheptulose and perseitol, in the dry matter is advantageously between 50 and 100%, more particularly between 65 and 90% by weight, in relation to the total weight of dry matter. The average analytical data for an aqueous solution containing 5% dry extract, obtained by the method described above, are given in the following table 2:

TABLE 2

| pH (¼ dilution) | 3-5 |
|---|---|
| C7 sugars/dry matter | 50-100% |

The relative composition of sugars of the water-soluble extract, by weight in relation to the total weight of dry matter of the extract, advantageously meets the following criteria (relative composition determined by HPLC):

| D-mannoheptulose | 0 to 100%, in particular 5 to 80%, |
|---|---|
| Perseitol | 0 to 100%, in particular 5 to 80%, |
| Sucrose | less than 10%, |
| Glucose | less than 10%, |
| Fructose | less than 10%. |

The water-soluble extract of avocado sugars includes advantageously, in relation to the total weight of dry matter, 10 to 80% by weight of D-mannoheptulose, more advantageously 15 to 70% by weight of D-mannoheptulose. The water-soluble extract of avocado sugars includes advantageously, in relation to the total weight of dry matter, 20 to 80% by weight of perseitol, more advantageously 25 to 70% by weight of perseitol.

Preferably, the relative composition of sugars of the water-soluble extract, by weight in relation to the total weight of dry matter of the extract, meets the following criteria (relative composition determined by HPLC):

| D-mannoheptulose | 25 to 60%, |
|---|---|
| Perseitol | 25 to 60%, |
| Sucrose | less than 10%, |
| Glucose | less than 10%, |
| Fructose | less than 10%. |

Surprisingly, the inventors have observed a synergistic effect between D-mannoheptulose and/or perseitol and the minor sugars (fructose, glucose, sucrose) present in the extract of avocado sugars.

The extract obtained may, optionally, be dried according to the processes known to the person of skills in the art by lyophilization or atomization, for example, with or without the help of a support such as maltodextrins, for example, with the aim of obtaining a solid powder (dry extract) that is completely water-soluble.

The extract obtained may, optionally, be fractionated into each purified sugar. This separation and purification can be performed by any of the techniques known to the person of skills in the art, among which mention may be made, in a non-exhaustive way, of precipitation/filtration, recrystallization, or separation by chromatography such as the improved simulated moving bed (ISMB) process.

According to a second advantageous variant of the invention, the C7 sugars, which are advantageously D-mannoheptulose and perseitol, are at least partially esterified with a —(CO)—R radical in which R represents a saturated or unsaturated hydrocarbon chain containing from 11 to 24 carbon atoms, optionally substituted by one or more substituents selected from the group comprised of hydroxy radicals (—OH), ethoxy radicals (—OC$_2$H$_5$) and the —SO$_3$M group with M representing a hydrogen atom, an ammonium ion (NH$_4^+$) or a metal ion. In particular, the C7 sugars are at least partially esterified with a fatty acid residue. The hydrocarbon chain may be linear or branched, and it is advantageously linear.

The radical R advantageously represents a fatty acid residue.

The fatty acids considered according to the invention are more particularly long-chain fatty acids i.e., those with more than 11 carbon atoms and notably more than 14 carbon atoms.

Their hydrocarbon chain may be saturated or contain one or more double bonds.

Examples of these fatty acids notably include saturated fatty acids such as palmitic (C$_{16}$), stearic (C$_{18}$), arachidic (C$_{20}$), behenic (C$_{22}$) and lignoceric (C$_{24}$) acids and unsaturated fatty acids such as palmitoleic (C$_{16}$), oleic (C$_{18}$), linoleic (C$_{18}$), linolenic, notably in its α and γ forms (C$_{18}$), and arachidonic (C$_{20}$) acids.

In particular, the R radical is advantageously selected from among the group comprised of a stearyl, linoleyl, oleyl, palmityl, lauryl, myristyl, arachidyl, behenyl, lauroleyl, myristoleyl, palmitoleyl, linolenyl in its α and γ forms, and/or arachidonyl radical.

It is particularly advantageous to substitute the hydrocarbon chain with a SO$_3$M group with M representing a hydrogen atom, an ammonium ion (NH$_4^+$) or a metal ion (in particular sodium).

In the derivatives of formula (I), the hydroxyl functional groups may be substituted by the residue of the same fatty acid or residues of different fatty acids.

The derivatives of fatty acids of C7 sugars may be obtained by an esterification reaction resulting from the contacting, under suitable conditions, of one or more acids of formula HOOC—R (R having the same definition as in the preceding paragraphs) with D-mannoheptulose and/or perseitol available commercially (synthetic origin) or with the water-soluble extract of avocado sugars described above.

According to a third advantageous variant of the invention, the C7 sugars, which are advantageously D-mannoheptulose and perseitol, are at least partially esterified with a —(CO)—R' radical in which R' represents a saturated or unsaturated hydrocarbon chain containing from 2 to 10 carbon atoms, optionally substituted by one or more substituents selected from the group comprised of hydroxy radicals (—OH), ethoxy radicals (—OC$_2$H$_5$) and the —SO$_3$M group with M representing a hydrogen atom, an ammonium ion (NH$_4^+$) or a metal ion. The hydrocarbon chain may be linear or branched, and it is advantageously linear.

The R radical advantageously represents a residue of a short-chain acid, i.e., one with fewer than 10 carbon atoms and notably fewer than 8 carbon atoms.

Their hydrocarbon chain may be saturated or contain one or more double bonds. As an example of these acids, notable mention may be made of acetic acid.

It is particularly advantageous to substitute the hydrocarbon chain with a SO$_3$M group with M representing a hydrogen atom, an ammonium ion (NH$_4^+$) or a metal ion (in particular sodium).

In the derivatives of formula (I), the hydroxyl functional groups may be substituted by the residue of the same acid or residues of different acids.

The derivatives of acids of C7 sugars may be obtained by an esterification reaction resulting from the contacting, under suitable conditions, of one or more acids of formula HOOC—R' (R' having the same definition as in the preceding paragraphs) with D-mannoheptulose and/or perseitol available commercially (synthetic origin) or with the water-soluble extract of avocado sugars described above.

According to a fourth advantageous variant of the invention, the C7 sugars, which are advantageously D-mannoheptulose and perseitol, are at least partially esterified with a —(CO)—R radical and with a —(CO)—R' radical, R and R' having the same definitions as those given in the second and third variants.

The derivatives of acids of C7 sugars may be obtained by an esterification reaction resulting from the contacting, under suitable conditions, of one or more acids of formula HOOC—R and one or more acids of formula HOOC—R' with D-mannoheptulose and/or perseitol available commercially (synthetic origin) or with the water-soluble extract of avocado sugars described above.

The derivatives obtained by the second, third or fourth variants are called acid derivatives of D-mannoheptulose or of perseitol, respectively.

In any one of the second, third or fourth variants, the ratio between the number of ester functional groups of the compound of the formula (I) and the initial number of hydroxyl functional groups, or esterification rate, for a sugar molecule, varies from 0.2 to 1. It is notably less than or equal to 0.6, and in particular less than or equal to 0.4.

The degree of esterification is controlled by the concentration of the reagents, the duration of the reaction and the reaction temperature. It may be measured by chromatography, in particular by steric exclusion chromatography.

According to one or another of the four variants, the composition includes 0.001 to 30% by weight of D-mannoheptulose or the acid derivative thereof, in relation to the total weight of said composition, and/or 0.001 to 30% by weight of perseitol or the acid derivative thereof, in relation to the total weight of said composition. More particularly, the composition includes 0.002 to 5% by weight of D-mannoheptulose or the acid derivative thereof, in relation to the total weight of said composition, and/or 0.002 to 5% by weight of perseitol or the acid derivative thereof, in relation to the total weight of said composition.

The extract is advantageously used as an active agent in a composition such as a cosmetic, dermatological or pharmaceutical composition, which may include one or more suitable excipients. The composition may further include at least one other active compound in addition to C7 sugars. This other compound may be selected from among all the compounds and their functional equivalents, set forth below:

This other compound may be in particular selected from among the active agents typically used in dermatology or cosmetics such as emollients, moisturizing active agents, keratin synthesis activators, keratoregulators, keratolytics, agents that repair the cutaneous barrier, peroxisome proliferator-activated receptor (PPAR) agonists, RXR or LXR agonists, scarring agents, sebum-regulating agents, anti-irritation agents, soothing agents, anti-inflammatory agents, antioxidant agents and anti-aging agents, depigmenting or hypodepigmenting agents, pigmenting agents, lipolytic agents or lipogenesis inhibitors or anti-cellulitis or slimming agents, organic or inorganic sun screens or filters, antifungal compounds, preservatives, antibacterial agents, prebiotics and probiotics, antibiotics, and immunomodulators.

More particularly, the scarring agents and/or agents that repair the cutaneous barrier which can be used in combination are advantageously panthenol (vitamin B5), arabinogalactan, zinc oxide, ceramides, cholesterol, squalane and phospholipids.

The sebum-regulating agents that can be used in combination are advantageously selected from among the group comprised of 5-alpha-reductase inhibitors. Zinc (and zinc derivatives such as gluconate salts thereof, salicylate and pyroglutamic acid) and spironolactone also have sebum-suppressing activity. Other sebum-regulators of lipid origin acting on sebum quality, such as linoleic acid, are also of interest.

The anti-inflammatory and/or anti-irritation and/or soothing agent may be arabinogalactan.

The sun protection active agents that can be used in combination are advantageously UVB and/or UVA filters and sun screens, such as the inorganic and/or organic screens or filters known to persons skilled in the art, who will adapt their choice and their concentrations according to the degree of protection sought.

The preservatives that can be used in combination are, for example, those generally used in cosmetics, molecules with antibacterial activity (pseudo-preservatives) such as caprylic derivatives such as, for example, capryloyl glycine and glyceryl caprylate; hexanediol, sodium levulinate, and copper and zinc derivatives (gluconate and PCA).

This other compound may be in particular selected from among plant extracts, in particular:
  plant oils such as soy oil and/or rapeseed oil, avocado oil (WO2004/012496, WO2004/012752, WO2004/016106, WO2007/057439), lupin oil and advantageously sweet white lupin oil (WO98/47479), or a mixture of these oils;
  oleodistillate or concentrates of animal or plant oil, notably sunflower, more advantageously linoleic sunflower concentrates, such as the sunflower oil concentrated in unsaponifiables (Soline®—WO2001/21150), marketed by Laboratoires Expanscience, oils concentrated in unsaponifiables of the avocado, rapeseed and corn oil type useful notably for their moisturizing and/or emollient, healing and/or cutaneous barrier repair, anti-inflammatory and/or anti-irritation and/or soothing activity;
  unsaponifiables of plants or of plant oil, advantageously of avocado furans (Avocadofurane®), able to be obtained by the method described in the international application WO 01/21605, unsaponifiables of avocado and/or soy, more particularly a mixture of furanic unsaponifiables of avocado and unsaponifiables of soy, advantageously in a respective ratio of approximately 1/3-2/3 (such as Piascledine), the unsaponifiables of soy (such as obtained according to the method described in the international application WO 01/51596), sterolic unsaponifiables (typically unsaponifiables whose proportion of sterols, methylsterols and triterpene alcohol is between 20 and 95% by weight, preferably 45-65% by weight, in relation to the total weight of the unsaponifiable), phytosterols, esters of sterols and vitamin derivatives, notably useful for their healing and/or repair of the cutaneous barrier, anti-aging or anti-inflammatory activity;
  peptides or complexes of plant amino acids, in particular of avocado (such as those described in the international application WO 2005/105123), lupin peptides (such as those described in the international application WO 00/62789), total extract of lupin (such as those described in the international application WO 2005/102259), quinoa peptides (such as those described in the international application WO 2008/080974), maca peptides (such as those described in the international application WO 2004/112742), fermented or non-fermented soy peptides, rice peptides (such as those described in the international application WO 2008/009709), useful notably for their moisturizing and/or emollient (avocado), keratoregulating (lupin, quinoa), healing and/or barrier repairing (maca, quinoa, soy), anti-inflammatory and/or anti-irritation and/or soothing (lupin, quinoa), antioxidant (avocado), anti-aging (lupin, maca) and pigmenting activity (rice), *Schisandra* peptides (such as those described in the patent application FR 0955344), extract of seeds of *Acacia macrostachya* (such as that described in the patent application FR 0958525), extract of seeds of *Vigna unguiculata* (such as that described in the patent application FR 0958529); extract of seeds of *Passiflora* (such as that described in the patent application FR 1262234);
  butyl avocadate (5 alpha Avocuta®), 5-alpha reductase inhibitor (WO 01/52837 and WO 02/06205) and typically, regulator of the seborrheic secretions found increased in acne and in dandruff;
  polyphenol-rich extracts, and more particularly extracts of avocado fruits (such as those described in the application FR 1 061 055), extracts of maca leaves (such as those described in the application FR 1 061 047), and extracts of the aerial parts of *Gynandropsis gynandra* (such as those described in the application FR 1 061 051),
  lupeol (FR 2 822 821, FR 2 857 596) useful notably to promote scarring;
  cupuaçu butter, particularly appreciated for its moisturizing properties.

This other compound may be in particular selected from among oxazolines, in particular those selected from among the group comprised of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline (preferably 2-undecyl-4,4-dimethyl-1,3-oxazoline, called the OX-100 or Cycloceramide®; WO 2004050052, WO 2004050079 and WO 2004112741). They are particularly useful for their anti-inflammatory and/or anti-irritation and/or soothing, antioxidant, depigmenting, immunomodulatory activity.

C7 sugars may also be combined with compounds that protect or activate stem cells such as Stemoxydine® (diethyl pyridine-2,4-dicarboxylate), Survicode™ (sodium cocoyl alaninate), Survixyl IS™ (pentapeptide-31), Defensil® (ctyldodecanol, Echium Planta-gineum Seed Oil, Cardiospermum Halicacabum Flower/Leaf/Vine Extract, *Helianthus Annuus* Sun-flower Seed Oil Unsaponifiables), Celligent® (*Helianthus Annuus* Sunflower Seed Oil, Ethyl Ferulate, Polyglyceryl-5 Trioleate, *Rosmarinus Officinalis* Leaf Extract, Aqua, Disodium Uridine Phosphate), Phycosaccharide AI® (alginic acid, sodium salt, hydrolyzed), Phycojuvenine® (*Laminaria digitata* extract), PhytoCellTec™ containing extract of plant stem cells of Apline rose or Gamay Freaux teinturier grape or Uttwiler spatlauber apple (*Malus domestica*) or argan, plant stem cells extracted from *Vitis vinifera* vines, plant stem cells of Christe Marine shoots.

All of these combinations include at least one other active compound, in addition to C7 sugars, and may include two, three, four or more active compounds as described above.

The composition according to the invention may be formulated in the form of various preparations suitable for topical, oral, rectal, vaginal, nasal, auricular or bronchial administration, as well as to parenteral administration.

According to a first variant, the various preparations are suitable for topical administration and notably include creams, emulsions, milks, pomades, lotions, oils, aqueous or water-alcohol or glycolic solutions, powders, patches, sprays, shampoos, varnishes or any other product for external application.

The composition including C7 sugars having the specifications indicated is particularly intended for cosmetic, pharmaceutical, dermatological or nutraceutical use.

In the context of cosmetic, pharmaceutical or dermatological use, the composition will advantageously be formulated in the form of a preparation suitable for topical administration. The composition including a peptide and sugar extract is particularly intended for cosmetic, pharmaceutical or dermatological use.

In the context of dietary use, with nutritive or cosmetic aims ("cosmet-food"), the composition will advantageously be formulated in the form of a preparation suitable for oral administration.

The invention also has as an object the use of C7 sugars for the manufacture of a cosmetic, pharmaceutical, dermatological or nutraceutical composition, or a functional food.

A functional food is a conventional food, or one that appears as such, which is part of a normal diet and which has as a characteristic to provide beneficial physiological effects that exceed its typical nutritional functions or to reduce the risk of chronic diseases.

The invention thus relates to a functional food including the extract according to the invention.

The invention also relates to an extract according to the invention or a composition according to the invention for its use to prevent and/or treat:
- disorders or pathologies of the skin and/or the mucous membranes and/or epithelial appendages
- vascular disorders
- deteriorations in adipose tissue.

In particular, the composition or extract according to the invention is intended for the prevention and/or treatment of allergic, inflammatory or irritating reactions or pathologies or scarring disorders or disorders of the barrier or the homeostasis of the skin, epithelial appendages (hair and nails) and/or mucous membranes (gums, periodontium, genital mucosa) whether immature, normal or mature/aged.

Advantageously, the composition or extract according to the invention may be used for the prevention and/or treatment of reactions, disorders or pathologies of the:

skin, such as acne, rosacea or erythrocouperosis, psoriasis, vascular disorders, diaper rash, atopic dermatitis, eczema, contact dermatitis, irritative dermatitis and in particular irritative diaper rash, allergic dermatitis, seborrheic dermatitis (cradle cap), psoriasis, Leiner's disease, sensitive skin, reactive skin, dry skin (xerosis), dehydrated skin, skin damaged by the sun, radiation, wind, cold, heat, stress, pollution, impetigo, skin with redness, cutaneous erythema, aged or photoaged skin, photosensitized skin, pigmented skin (melasma, postinflammatory pigmentation, etc.), depigmented skin (vitiligo), skin with cellulitis, loose skin, skin with stretch marks, dry patches, angiomas, hemangiomas, ichthyoses, chapping, punctures, cracks, in particular of the breasts, burns, sunburn, inflammations due to rays of all types, irritations by chemical, physical (for example pressure stress for expectant mothers), bacteriological, fungal or viral, parasitic (lice, scabies, tinea, mites, dermatophytes, warts, prurigo strophulus, mycoses such as candidiasis and pityriasis) or radiological agents, or by a deficit in innate immunity (antimicrobial peptides) or acquired immunity (cellular, humoral, cytokines), and/or mucous membranes such as the gums and periodontium able to have gingivitis (sensitive gums of newborns, problems of hygiene, the use of tobacco or others), periodontopathies, or genital mucosa presenting irritations of the external or internal male or female genitalia, and/or epithelial appendages such as the nails (breakable, fragile nails, etc.) and hair (alopecia, dandruff, hirsutism, seborrheic dermatitis, folliculitis) immature, normal or mature, presenting in particular disorders of the scalp such as androgenetic, acute, localized, cicatricial and congenital alopecia, occipital alopecia of infant and alopecia areata, due to chemotherapy/radiotherapy or telogen effluvium, anagen effluvium, pilar dystrophy, trichotillomania, tinea or oily or dry dandruff.

The invention also relates to a method of cosmetic care of the skin and/or epithelial appendages and/or mucous membranes, in order to improve their state and/or their appearance, consisting in administering a composition or extract according to the present invention.

The invention relates to a method of cosmetic care of the skin, in order to prevent its aging, consisting in applying to the skin a composition or extract according to the present invention.

The composition or extract according to the present invention may also be advantageously used in the prevention and/or treatment of scarring disorders.

The composition or extract according to the present invention may also be advantageously used in the prevention and/or treatment of vascular disorders, in particular redness and blotches.

The composition or extract according to the present invention may also be advantageously used in the prevention and/or treatment of deteriorations of adipose tissue. Deteriorations in adipose tissue are in particular cellulitis or the "orange skin" effect. The composition according to the invention makes it possible to tone the skin.

The modes of administration, dosing schedules and the optimal galenic forms of the compounds and compositions according to the invention may be determined according to the criteria generally taken into account in the establishment of a pharmaceutical treatment, in particular a dermatological, cosmetic or veterinary treatment suitable for a patient or an animal, such as for example the age or the body weight of the patient or animal, the severity of its general condition, tolerance to the treatment, noted side effects and skin type. Depending on the type of administration desired, the active composition and/or compounds according to the invention may further include at least one pharmaceutically acceptable excipient, in particular a dermatologically acceptable excipient, or a cosmetically acceptable excipient. According to the first variant, an excipient suitable for administration by external topical route is used. The composition according to the present invention may further include at least one pharmaceutical or cosmetic adjuvant known to persons skilled in the art, selected among from thickeners, preservatives, fragrances, colorants, chemical or inorganic filters, moisturizing agents, thermal spring waters, etc.

FIGURE LEGENDS

FIG. 1: Evolution of genes of stem cells in the presence of avocado perseose.

Figure 2:
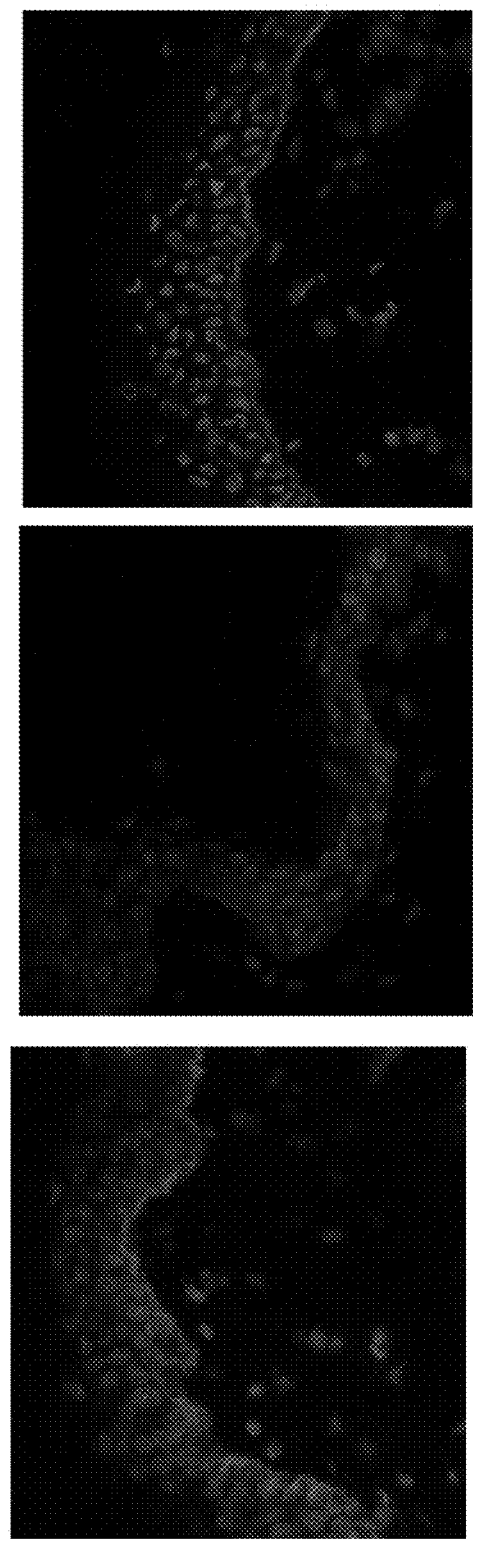

FIG. 2: Immunostaining of integrin alpha 6, marker for basal layer stem cells; A: control not irradiated or treated; B: UVA+UVB irradiation; C: UVA+UVB irradiation in the presence of avocado perseose.

Figure 3:
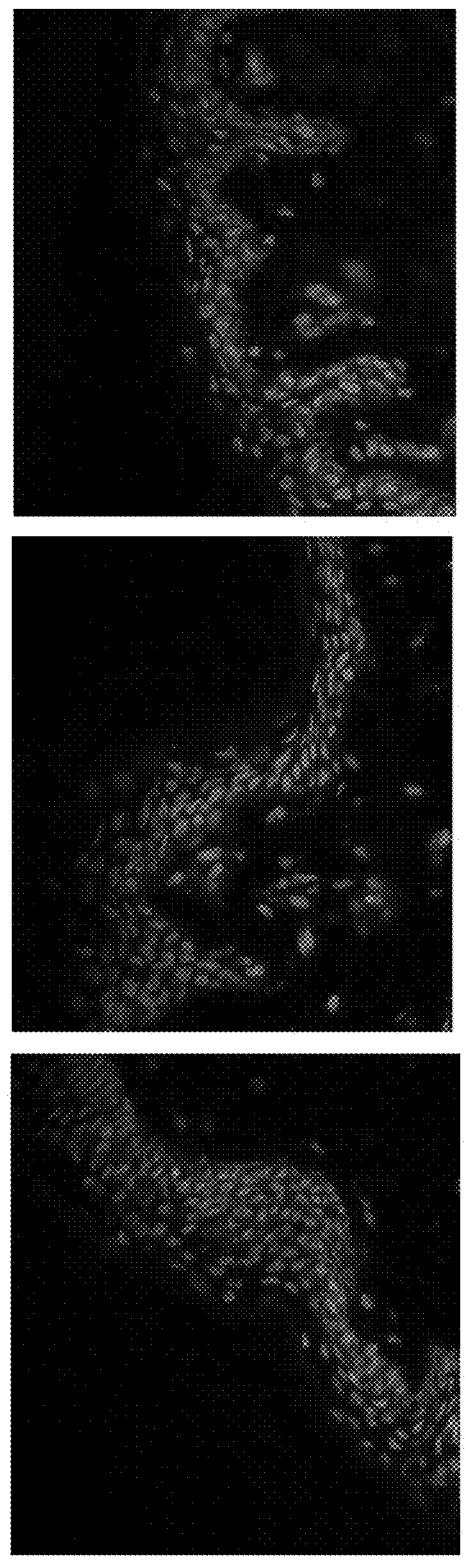

FIG. 3: Immunostaining of integrin beta 1, marker for basal layer stem cells; A: control not irradiated or treated; B: UVA+UVB irradiation; C: UVA+UVB irradiation in the presence of avocado perseose.

The examples which follow illustrate the invention but are not restrictive.

EXPERIMENTAL EXAMPLES

1. Example 1: Preparation of a Water-Soluble Extract of Avocado Sugars

Fresh avocados, of the Hass variety, are cut into thin slices 2-5 mm thick, seed included, using a circular-blade slicer. The drying apparatus is a temperature controlled hot air drying oven. The sliced avocados are distributed in a thickness of 4-5 cm on stacked racks. Drying is for 48 hours at a temperature of 80° C. Once dried, the fruits are subjected to cold pressing. This operation is carried out on a small Komet® laboratory press. Thus, oil and oil cake are obtained.

The oil cake is then crushed and then extracted, in the presence of 70% ethanol or water.

The liquid and solid portions are separated by centrifugation, for example. The soluble fraction (liquid) is taken up to be purified and concentrated according to the following procedure:

Demineralization using ion-exchange resins: demineralization of heptuloses by passing over OH⁻ resins and then over H⁺ resin.

Ultrafiltration at 10,000 Da: ultrafiltration is carried out with a system equipped with four 10 kDa cut-off membranes.

Vacuum concentration: the purified extract is concentrated using a vacuum evaporator until a dry matter content of near 4% is obtained.

Packaging: the concentration of the extract is adjusted to 5% dry matter and preservative is added, and then it is sterile filtered on a 0.2 μm cut-off membrane and packaged.

Table 3 gives the composition of the extract of avocado C7 sugars, with 5% dry matter, prepared according to the method described above:

TABLE 3

| Appearance<br>Analytical criteria | Pale yellow solution |
|---|---|
| Dry matter | 5% |
| pH (¼ dilution) | 7.0 |
| Composition (%/dry matter) | |
| Sucrose | 3.0 |
| Glucose | 7.5 |
| D-mannoheptulose | 40.0 |
| Fructose | 8.6 |
| Perseitol | 40.0 |

According to this same method, two other extracts were prepared, whose pH, absorbance and C7 sugar content values in are given in table 4. The C7 sugar content corresponds to the sum of perseitol and D-mannoheptulose analyzed by HPLC.

TABLE 4

| | Batch | |
|---|---|---|
| | 1 | 2 |
| Dry matter | 5% | 5% |
| pH (¼ dilution) | 5.9 | 5.4 |
| C7 sugars/dry matter | 80.5 | 83.4 |

The avocado sugars prepared by the method of example 1 and called "avocado perseose" hereafter were used to study the expression of stem cell markers under various conditions.

2. Effect of Avocado Perseose on the Expression Profile of Stem Cell Genes and Markers The effect of avocado perseose on the expression of stem cell markers was first tested in a keratinocyte culture model.

2.1. Materials and Methods 2.1.1. Biological Model and Treatment

Skin samples were taken (from circumcision or mammaplasty, according to the sex of the donor) from donors aged from 1 month, 3 months, 3 years, 6 years and 11 years, as well as from adults. From these skin samples, epidermal keratinocytes were extracted and grown in supplemented SFM, at 37° C. and 5% $CO_2$.

The various keratinocytes were grown for 24 hours. After incubation, the medium was replaced by medium containing 0.005% avocado perseose or not (control). The cells were then incubated for 24 hours. All the experimental conditions were carried out in triplicate. At the end of incubation, the culture supernatants were removed and the cell layers were immediately freeze dried at −80° C.

2.1.2. Analysis of the Differential Expression of Genes of Interest

The expression of markers was evaluated by RT-qPCR on the messenger RNA extracted from the cell layers of each donor. Total RNA was extracted from each sample using TriPure Isolation Reagent® (Roche) according to the protocol recommended by the manufacturer. The extracted RNA was quantified using the NanoVue™ spectrophotometer (GE Healthcare). For the analysis by quantitative RT-PCR (RT-qPCR), the prepared RNA was first reverse-transcribed into cDNA in the presence of oligo(dT) using the Superscript II enzyme. The cDNA obtained was quantified using the NanoVue™ spectrophotometer (GE Healthcare) and their concentration adjusted to 5 ng/μl.

The PCR reactions were carried out by quantitative PCR with the "Light Cycler" system (Roche Molecular Systems Inc.) according to the procedures recommended by the supplier.

The reaction mixture (10 μl final) for each sample contains 2.5 μl of 5 ng/μl cDNA, the primers for the various markers used, the reaction mixture (Roche) containing Taq DNA polymerase enzyme, SYBR Green I marker and $MgCl_2$.

The incorporation of fluorescence into the amplified DNA is measured continuously during PCR cycles. These measurements make it possible to obtain fluorescence intensity curves as a function of PCR cycles and to thus evaluate a value of relative expression for each marker.

The number of cycles is determined from the exit points of the fluorescence curves. For a given marker used, the later a sample leaves (high number of cycles), the lower the initial number of copies of mRNA.

The relative expression (RE) value is expressed in arbitrary units according to the following formula:

$$RE = (1/2^{number\ of\ cycles}) \times 10^6$$

The reference gene for stable expression regardless of the experimental conditions, which makes it possible to normalize the results is GAPDH.

2.2. Results

Genomic analysis showed that the expression of genes of stem cells, KRT15, NOTCH1, KRT19, ITGBP1 and ITGA6, is high after birth and decreases with age. This expression profile was maintained in the presence of avocado perseose (FIG. 1), demonstrating that avocado perseose is well tolerated by cells.

3. Evaluation of the Protective Effect of Epidermal Stem Cells from Avocado Perseose with Respect to UVA+UVB Irradiation The protective effect of avocado perseose on stem cell markers was tested with a model of skin irradiated with UV or not irradiated.

3.1. Materials and Methods 3.1.1. Biological Model and Treatment

Skin explants are allowed to stabilize for 4 hours at 37° C. in DMEM with 5% serum.

The explants are placed in a 24-well plate containing DMEM with 5% serum. The skin samples are pretreated with 0.01% avocado perseose applied topically to the center of the explant. PBS is deposited on the untreated explants considered as controls.

The skin samples are also pretreated with 0.005% avocado perseose in the culture medium. Each condition is evaluated in duplicate. The skin samples are left in the oven for 24 hours. The explants are rinsed with PBS and then transferred to 6-well lates to be irradiated. The irradiation dose is 10 $J/cm^2$ in UVA and 200 $mJ/cm^2$ in UVB.

The explants are treated again as before and then returned to the incubator for 24 hours.

3.1.2. Protein Immunostaining within Tissue

The inclusion technique preserves the biopsy in a frozen state without chemical fixing (which could alter the epitopes of the antigens of interest). The inclusion of skin is carried out in two steps: a step of molding the skin in a histocassette filled with OCT (Tissue-Tek), a substance that makes it possible to preserve skin biopsies in frozen form in order to prepare sections with a cryostat. And a second step in liquid nitrogen makes it possible to freeze and harden the preparation. Next, 10 μm sections are prepared with a cryostat (a refrigerated enclosure for preparing frozen sections on a microtome). The sections of skin mounted on microscope slides are fixed in acetone for 10 minutes. The nonspecific sites are saturated. The primary antibodies (anti-Δp63α, anti-α6 and anti-β1) are left to incubate overnight at 4° C. Then the signal is developed with the secondary antibodies coupled to a fluorochrome for 1 hour at room temperature in the dark. At the same time as this incubation, the cell nuclei are stained with DAPI.

The skin samples are observed by fluorescence optical microscopy using the Olympus CK 40 microscope. Visualization of the fluorescence employs the filters Rhodamine (TRITC, red), FITC (green) and Dapi (blue). The skin samples are observed under 40× magnification. The image acquisition software is called Archimed (Microvision).

The images were acquired with an automated high-resolution imaging system (INCell Analyzer™1000, GE Healthcare). For each condition, two skin explants were analyzed and five digital images were captured per explant, for a total of 10 analyzed images.

3.2. Results

Staining was quantified by measuring the intensity of fluorescence of integrin alpha 6 in relation to the number of nuclei identified by DAPI.

As indicated in table 5, the cells that were irradiated lost the expression of integrin alpha 6. On the other hand, the expression of this marker is maintained when the cells are treated with avocado perseose, indicating that avocado perseose makes it possible to preserve the potential of epidermal stem cells.

TABLE 5

Quantification of the staining of integrin alpha 6 in the basal layer of skin explants

|  | INTEGRIN ALPHA 6 (fluorescence intensity | % in relation to the control |
|---|---|---|
| Control not irradiated or treated | 49854 | 100% |
| UVA + B irradiation | 10103 | 20% |
| Avocado perseose - UVA + B irradiation | 40021 | 80% |

4. Examples of Formulations 4.1. Moisturizing Cream

TABLE 6

| Raw material/Trade name | % |
|---|---|
| CAPRYLO CAPRATE GLYC | 1 to 15% |
| SUNFLOWER OIL SR | 1 to 15% |
| PURE CETYL ALCOHOL | 1 to 5% |
| GLYCERYL STEARATE CITRATE | 1 to 10% |
| BEESWAX | 1 to 5% |
| EUMULGIN SG | 0 to 2% |
| VITAMIN E ACETATE | 0 to 1% |
| PURIFIED WATER | QSP 100% |
| CARBOPOL ULTREZ 20 | 0 to 1% |
| GLYCEROL | 1 to 10% |
| XANTHAN GUM | 0 to 1% |
| SOUDEXI DETERGENT | 0 to 1% |
| PRESERVATIVE | 0 to 2% |
| AVOCADO PERSEOSE | 0 to 1% |

4.2. Restructuring Milk

TABLE 7

| Raw material/Trade name | % |
| --- | --- |
| PURIFIED WATER | QSP 100% |
| SUNFLOWER OIL SR | 1 to 10% |
| HYDRO COPRA OIL | 1 to 10% |
| SWEET ALMOND OIL | 1 to 10% |
| CORN OIL | 1 to 10% |
| MONOSTEARATE GLYCEROL | 1 to 10% |
| STEARIC ACID | 1 to 10% |
| PRESERVATIVE | 0 to 2% |
| C16-C18 CETYL ALCOHOL | 0 to 2% |
| VITAMIN E ACETATE | 0 to 1% |
| SOUDEXI DETERGENT | 0 to 1% |
| AVOCADO PERSEOSE | 0 to 1% |

4.3. Cleansing Water

TABLE 8

| Raw material/Trade name | % |
| --- | --- |
| PURIFIED WATER | QSP 100% |
| GLYCEROL | 1 to 10% |
| SODIUM COCOYL GLUTAMATE | 1 to 10% |
| PRESERVATIVE | 0 to 2% |
| RICINUS HYDROBUTETH 26 | 0 to 2% |
| ALLANTOIN | 0 to 2% |
| TARTARIC ACID | 0 to 2% |
| *ALOE VERA* POWDER SR | 0 to 2% |
| SOAPWORT EXTRACT SR | 0 to 2% |
| SOUDEXI DETERGENT | 0 to 2% |
| AVOCADO PERSEOSE | 0 to 1% |

4.4. Shampoo

TABLE 9

| Raw material/Trade name | From |
| --- | --- |
| PURIFIED WATER | QSP 100% |
| COCAMIDOPROPYL BETAINE | 1 to 10% |
| GLYCEROL | 1 to 10% |
| COCOGLUCOSIDEXI | 1 to 10% |
| SODIUM MYRETH SULFATE | 1 to 10% |
| PRESERVATIVE | 0 to 2% |
| PEG6000 DISTEARATE | 0 to 2% |
| POLYQUARTERNIUM JR400XI | 0 to 2% |
| DEXTROROTATORY PANTHENOL | 0 to 2% |
| HYDXI A CITRIC CID | 0 to 2% |
| AVOCADO PERSEOSE | 0 to 1% |

4.5. SPF 50+ Sun Cream

TABLE 10

| Raw material/Trade name | From |
| --- | --- |
| COPRAH CAPRYLATE/CAPRATE | 5 to 20% |
| DICAPRYLYL CARBONATE | 5 to 20% |
| CAPRYLOCAPRATE GLYC | 5 to 20% |
| MIGLYOL GELB | 5 to 20% |
| TITANDIOXID JOJOBA ESTERS | 1 to 15% |
| TINOSORBS | 1 to 5% |
| DIETAMIN HYDBENZO YHEXBENZ | 1 to 10% |
| ETHYL HEXYL TRIAZONE | 1 to 10% |
| HAREF AVOCADO OIL | 1 to 5% |
| ALPHA TOCOPHEROL | 0.05 to 1% |
| LAURYL GLUCOSE-GLYSTEARATXI | 2 to 12% |
| PURIFIED WATER | QSP 100% |
| GLYCEROL | 1 to 10% |
| XANTHAN GUM | 0 to 1% |
| PRESERVATIVE | 0 to 2% |
| POTASSIUM CETYL PHOSPHATE | 0 to 2% |
| SOUDEXI DETERGENT | 0 to 2% |
| PHENYL BENZIMIDAZO SULFONAC | 1 to 5% |
| AVOCADO PERSEOSE | 0 to 1% |

The invention claimed is:

1. A method for treating skin cancer, consisting essentially of administering to a subject in need thereof an effective amount of a composition consisting essentially of at least one C7 sugar or derivative of the following formula (I)

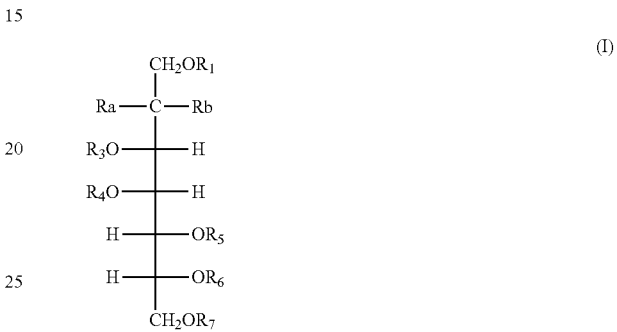

wherein
Ra is a hydrogen atom and Rb is an —OR$_2$ or CRaRb represents the CO radical;
R$_1$, R$_2$, R$_3$, R$_4$, R$_5$, R$_6$ and R$_7$ are, independently of one another
a hydrogen atom or
a —(CO)—R radical in which R is a saturated or unsaturated hydrocarbon chain containing from 11 to 24 carbon atoms, optionally substituted by one or more substituents selected from the group consisting of hydroxy radicals (—OH), ethoxy radicals (—OC$_2$H$_5$) and the —SO$_3$M group, wherein M is a hydrogen atom, an ammonium ion (NH$_4^+$) or a metal ion; or
a —(CO)—R' radical in which R' is a saturated or unsaturated hydrocarbon chain containing from 2 to 10 carbon atoms, optionally substituted by one or more substituents selected from the group consisting of hydroxy radicals (—OH), ethoxy radicals (—OC$_2$H$_5$) and the —SO$_3$M group, wherein M is a hydrogen atom, an ammonium ion (NH$_4^+$) or a metal ion; and
wherein the degree of esterification, for a sugar molecule, is between 0.2 and 1;
and a pharmaceutically acceptable excipient, wherein said composition protects epidermal stem cells,
wherein said stem cells are basal stem cells, and
wherein said subject is a child.

2. The method of claim 1, wherein skin barrier function is maintained.

3. The method of claim 1, wherein aging of the skin is reduced.

4. The method of claim 1, wherein said composition promotes wound healing.

5. The method of claim 1, wherein expression of one or more stem cell markers is maintained.

6. The method of claim 5, wherein said marker is selected from the group consisting of ΔNp63, FN1 (fibronectin 1), MCSP (melanoma-associated chondroitin sulfate proteoglycan), LRIG1 (leucine-rich repeats and immunoglobulin-like domains protein 1), GJA1 (connexin 43), NID1 (nidogen 1), NOTCH1 (Notch homolog 1, translocation-associated), KRT15 (keratin 15), KRT19 (keratin 19), EGFR (epidermal growth factor receptor), CD71 (transferrin receptor), DSG3 (desmoglein 3), ITGB1BP1 (integrin beta 1 binding protein), ITGA6 (integrin alpha 6) and ITGB4 (integrin beta 4).

7. The method of claim 5 wherein said marker is ITGA6 (integrin alpha 6).

8. The method of claim 1, wherein R is a fatty acid residue.

9. The method of claim 8, wherein the fatty acid residue is selected from the group consisting of a stearyl, linoleyl, oleyl, palmityl, lauryl, myristyl, arachidyl, behenyl, lauroleyl, myristoleyl, palmitoleyl, linolenyl in its α and γ forms, and/or arachidonyl radical.

10. The method of claim 1, wherein the composition includes a C7 sugar selected from the group consisting of mannoheptulose, perseitol and mixtures thereof.

11. The method of claim 1, wherein said composition includes 0.001 to 30% by weight D-mannoheptulose or an acid derivative thereof, in relation to the total weight of said composition, and/or 0.001 to 30% by weight perseitol or an acid derivative thereof, in relation to the total weight of said composition.

12. The method of claim 10, wherein the source of mannoheptulose and/or perseitol is a water-soluble extract of avocado sugars.

13. The method of claim 12, wherein the avocado sugar water-soluble extract is obtained by a method comprising the following steps in the order shown:

drying and extracting lipids to obtain an avocado oil cake;

cryogrinding and total delipidation of said oil cake, then decanting and centrifugation in order to recover a soluble fraction rich in C7 sugars (elimination of the cake);

demineralization on ionic resin of said soluble fraction obtained in the preceding step;

ultrafiltration at 10,000 daltons; and concentration under vacuum and packaging.

14. The method of claim 13, wherein the avocado oil cake is obtained from avocado fruit.

15. The method of claim 13, wherein the water-soluble extract of avocado sugars includes by weight, in relation to the total weight of dry matter of the extract (relative composition determined by HPLC):

| D-mannoheptulose | 5 to 80% |
| Perseitol | 5 to 80% |
| Sucrose | less than 10% |
| Glucose | less than 10% |
| Fructose | less than 10%. |

16. The method of claim 1, wherein said composition is administered topically or orally.

17. A method for treating skin cancer, consisting essentially of administering to a subject in need thereof an effective amount of a composition consisting essentially of at least one C7 sugar or derivative of the following formula (I)

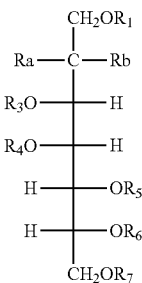

and one additional active agent;
wherein
Ra is a hydrogen atom and Rb is an —OR$_2$ or CRaRb represents the CO radical;

R$_1$, R$_2$, R$_3$, R$_4$, R$_5$, R$_6$ and R$_7$ are, independently of one another
a hydrogen atom or
a —(CO)—R radical in which R is a saturated or unsaturated hydrocarbon chain containing from 11 to 24 carbon atoms, optionally substituted by one or more substituents selected from the group consisting of hydroxy radicals (—OH), ethoxy radicals (—OC$_2$H$_5$) and the —SO$_3$M group, wherein M is a hydrogen atom, an ammonium ion (NH$_4$+) or a metal ion; or
a —(CO)—R' radical in which R' is a saturated or unsaturated hydrocarbon chain containing from 2 to 10 carbon atoms, optionally substituted by one or more substituents selected from the group consisting of hydroxy radicals (—OH), ethoxy radicals (—OC$_2$H$_5$) and the —SO$_3$M group, wherein M is a hydrogen atom, an ammonium ion (NH$_4$+) or a metal ion;
wherein at least one of the hydroxyl groups is esterified;
and a pharmaceutically acceptable excipient, wherein said composition protects epidermal stem cells,
wherein said stem cells are basal stem cells,
wherein said subject is a child, and
wherein said additional active agent is:
a dermatological active agent selected from the group consisting of emollients, moisturizing active agents, keratin synthesis activators, keratoregulators, keratolytics, agents that repair the cutaneous barrier, peroxisome proliferator-activated receptor (PPAR) agonists, RXR or LXR agonists, scarring agents, sebum-regulating agents, anti-irritation agents, soothing agents, anti-inflammatory agents, antioxidant agents and anti-aging agents, depigmenting or hypodepigmenting agents, pigmenting agents, lipolytic agents or lipogenesis inhibitors or anti-cellulitis or slimming agents, organic or inorganic sun screens or filters, antifungal compounds, preservatives, antibacterial agents, prebiotics and probiotics, antibiotics, immunomodulators and mixtures thereof;
selected from the group consisting of prebiotics and probiotics, antibacterial agents, antifungal compounds, preservatives, immunomodulators, growth factors, and mineral or organic sun filters or screens (pigmentary or ultrafine);
selected from the group consisting of wound-healing agents and/or agents that repair the cutaneous barrier, anti-inflammatory and/or anti-irritations and/or soothing agents, sebum-regulating agents, anti-inflammatory and/or anti-irritations and/or soothing agents, hypopigmenting or depigmenting agents, inorganic or organic sun filters and screens, and preservatives;

selected from the group consisting of plant oils, oleodistillates or concentrates of plant or animal oil, unsaponifiables of plants or plant oil, peptides or complexes of plant amino acids, butyl avocadate, extracts rich in polyphenols, lupeol, Cupuacu butter, oxazolines, and mixtures thereof; or selected from the group consisting of diethyl pyridine-2,4-dicarboxylate, sodium cocoyl alaninate, pentapeptide-31, ctyldodecanol, Echium Plantagineum Seed Oil, Cardiospermum Halicacabum Flower/Leaf/Vine Extract, *Helianthus Annuus* Sunflower Seed Oil Unsaponifiables, *Helianthus Annuus* Sunflower Seed Oil, Ethyl Ferulate, Polyglyceryl-5 Trioleate, *Rosmarinus Officinalis* Leaf Extract, Aqua, Disodium Uridine Phosphate, hydrolyzed alginic acid, extracts of *Laminaria digitata*, extracts of plant stem cells of Apline rose, extracts of plant stem cells of Gamay Freaux teinturier grape, extracts of plant stem cells of Uttwiler spatlauber apple (*Malus domestica*), extracts of plant stem cells of argan, extracts of plant stem cells of *Vitis vinifera* vines, and plant stem cells of Christe Marine shoots.

18. The method of claim 17, wherein said composition is administered topically or orally.

19. The method of claim 17, wherein skin barrier function is maintained.

20. The method of claim 17, wherein aging of the skin is reduced.

21. The method of claim 17, wherein said composition promotes wound healing.

22. The method of claim 17, wherein expression of one or more stem cell markers is maintained.

23. The method of claim 22, wherein said marker is selected from the group consisting of ΔNp63, FN1 (fibronectin 1), MCSP (melanoma-associated chondroitin sulfate proteoglycan), LRIG1 (leucine-rich repeats and immunoglobulin-like domains protein 1), GJA1 (connexin 43), NID1 (nidogen 1), NOTCH1 (Notch homolog 1, translocation-associated), KRT15 (keratin 15), KRT19 (keratin 19), EGFR (epidermal growth factor receptor), CD71 (transferrin receptor), DSG3 (desmoglein 3), ITGB1BP1 (integrin beta 1 binding protein), ITGA6 (integrin alpha 6) and ITGB4 (integrin beta 4).

24. The method of claim 22 wherein said marker is ITGA6 (integrin alpha 6).

25. The method of claim 17, wherein the degree of esterification, for a sugar molecule, is between 0.2 and 1.

26. The method of claim 17, wherein R is a fatty acid residue.

27. The method of claim 26, wherein the fatty acid residue is selected from the group consisting of a stearyl, linoleyl, oleyl, palmityl, lauryl, myristyl, arachidyl, behenyl, lauroleyl, myristoleyl, palmitoleyl, linolenyl in its α and γ forms, and/or arachidonyl radical.

28. The method of claim 17, wherein the composition includes a C7 sugar selected from the group consisting of mannoheptulose, perseitol and mixtures thereof.

29. The method of claim 17, wherein said composition includes 0.001 to 30% by weight D-mannoheptulose or an acid derivative thereof, in relation to the total weight of said composition, and/or 0.001 to 30% by weight perseitol or an acid derivative thereof, in relation to the total weight of said composition.

30. The method of claim 28, wherein the source of mannoheptulose and/or perseitol is a water-soluble extract of avocado sugars.

31. The method of claim 30, wherein the avocado sugar water-soluble extract is obtained by a method comprising the following steps in the order shown:

drying and extracting lipids to obtain an avocado oil cake;

cryogrinding and total delipidation of said oil cake, then decanting and centrifugation in order to recover a soluble fraction rich in C7 sugars (elimination of the cake);

demineralization on ionic resin of said soluble fraction obtained in the preceding step;

ultrafiltration at 10,000 daltons; and concentration under vacuum and packaging.

32. The method of claim 31, wherein the avocado oil cake is obtained from avocado fruit.

33. The method of claim 31, wherein the water-soluble extract of avocado sugars includes by weight, in relation to the total weight of dry matter of the extract (relative composition determined by HPLC):

| | |
|---|---|
| D-mannoheptulose | 5 to 80% |
| Perseitol | 5 to 80% |
| Sucrose | less than 10% |
| Glucose | less than 10% |
| Fructose | less than 10%. |

* * * * *